United States Patent [19]

Ichimura et al.

[11] Patent Number: 5,688,998
[45] Date of Patent: Nov. 18, 1997

[54] SURFACE REFORMING AGENT, SURFACE REFORMING METHOD AND CONE-TYPE CALIX [4] RESORCINARENE COMPOUNDS

[75] Inventors: Kunihiro Ichimura; Eiichi Kurita, both of Yokohama; Masahide Ueda, Tokuyama, all of Japan

[73] Assignee: Toda Kogyo Corporation, Japan

[21] Appl. No.: 401,499

[22] Filed: Mar. 10, 1995

[30] Foreign Application Priority Data

Mar. 11, 1994 [JP] Japan ................................ 6-067756
Mar. 11, 1994 [JP] Japan ................................ 6-067757

[51] Int. Cl.[6] ............................. C07C 31/18; C07C 57/40
[52] U.S. Cl. ............................................. 562/466; 568/633
[58] Field of Search ........................... 568/719, 640, 568/633; 562/508, 466

[56] References Cited

U.S. PATENT DOCUMENTS

| | | | |
|---|---|---|---|
| 4,695,615 | 9/1987 | Leonard et al. | 526/209 |
| 5,218,060 | 6/1993 | Rolfe et al. | 525/507 |

FOREIGN PATENT DOCUMENTS 0409403  1/1991  European Pat. Off. .

OTHER PUBLICATIONS

Wang, J.; Liu, J. "Calixarene–coated amperometric detectors"; Anal. Chim. Acta (1994), 294(2), pp. 201–206, Aug. 1994.

Aoyama, et al., *J. Am. Chem. Soc.*, "Molecular Recognition. 5.[1] Molecular Recognition of Sugars via Hydrogen–Bonding Interaction with a Synthetic Polyhydroxy Macrocycle[2]", 1989, 111, 5397–5404.

Patent Abstracts of Japan, vol. 17 No. 498 (P–1609) 8 Sep. 1993, & JP–A–05 127426, 25 May 1993. Abstracts.

S. Singh et al. "Bowl–shaped molecules as enzyme models", Journal of the Indian Medical Society Section B, vol. 29b, No. 7, Jul. 1990 New Delhi, IN, pp. 601–602.

W.C. Moreira et al. "Langmuir–Blodgett monolayers and vibrational spectra of calix [4] resorcinarene", p. 4149.

*Primary Examiner*—Donald R. Wilson
*Attorney, Agent, or Firm*—Nixon & Vanderhye

[57] ABSTRACT

The disclosure describes a surface reforming agent comprising a cone-type calix [4] resorcinarene compound represented by the formula (I):

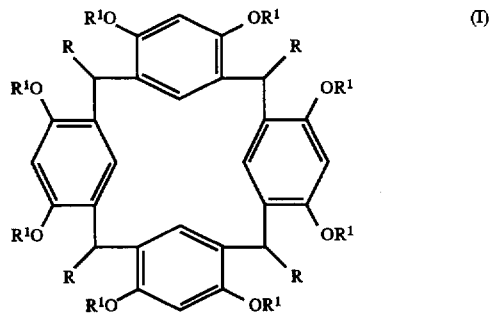

wherein R is an alkyl group having 3 to 18 carbon atoms, an alkenyl group having 3 to 18 carbon atoms, an aralkyl group having 3 to 18 carbon atoms or a substituted or non-substituted aryl group; $R^1$ is a hydrogen atom, a carboxyalkyl group in which the alkyl group has 1 to 3 carbon atoms, or a hydroxyalkyl group having 2 to 4 carbon atoms.

7 Claims, 4 Drawing Sheets

SURFACE REFORMING AGENT, SURFACE REFORMING METHOD AND CONE-TYPE CALIX [4] RESORCINARENE COMPOUNDS

BACKGROUND OF THE INVENTION

The present invention relates to a surface reforming agent, a surface reforming method using the same, and cone-type calix [4] resorcinarene compounds usable as an active ingredient of the surface reforming agent. More particularly, the present invention relates to a surface reforming agent capable of imparting the specific properties of cone-type calix [4] resorcinarene compounds comprising a cyclic resorcin tetramer to the surface of a material to be treated, that is, a surface reforming agent having a high adsorptivity, showing a strong adsorption and a high molecular orientability on the surface of a material to be treated, being capable of treating a variety of materials to be treated, and having a wide scope of application, a surface reforming method using the surface reforming agent, and cone-type calix [4] resorcinarene compounds usable as an active ingredient of the surface reforming agent.

The surface of a material is an important factor in the properties of the material. Many attempts have been made recently to modify the material surface by applying various surface reforming agents so as to improve or control the surface properties of the material such as electric charging properties, electroconductivity, anti-corrosiveness, hydrophilic or hydrophobic properties, etc. The importance of surface reforming is also pointed out in the field of designing of composite materials aimed at higher functional efficiency, as such surface reforming is essential for controlling the interface between the materials arisen by complexing.

In reforming the material surface for the purpose of improving surface properties or functionalizing the surface, a surface reforming agent capable of making a surface treatment with as a small quantity as possible and in a simple way is required. It is essential that such a surface reforming agent have a high adsorptivity owing to a number of adsorption sites in a molecule, be capable of forming a stable surface reforming layer due to the strong adsorption and also show a high molecular orientability in the material surface. Such a surface reforming agent is also required to be capable of application to a variety of materials to be treated.

Hitherto, surfactants and coupling agents have been popularly used for surface reforming treatment. For treatment of a material with a surfactant, methods are available in which the material to be treated is dipped in a surfactant solution, or a surfactant is added together with the material to be treated and mixed therein in the complexing process. The methods using a surfactant have the advantage of being simple and easy to carry out.

The surface reforming layer comprising a surfactant is formed by combining the hydrophilic portion of the surfactant with the surface of the material to be treated through hydrogen bond or Coulomb bond, and such linkage is reinforced by hydrophobic bonding between the long-chain alkyl groups.

The coupling agents are normally used for bonding between organic material and inorganic material. Silane coupling agents and titanate coupling agents are most popularly used. When using a silane coupling agent for forming a surface reforming layer, 1 to 3 alkoxy group(s) or chloride groups in the terminal silyl groups is chemically reacted with hydroxyl groups present in the material surface in the presence of water to form siloxane bonds which provide a solid reforming layer. Titanium coupling agents have a wide scope of application as they can be applied for surface treatment of a large variety of materials.

Thus, request is growing for a surface reforming agent which meets all of requirements, e.g., a high adsorptivity, a strong adsorption on object material, a high molecular orientability on the material surface, a capability of treating a large variety of materials and a wide scope of application, but no such agent has yet been available.

Regarding the surfactant, it should be noted that the adsorbing points of the surfactant molecules on the material surface greatly depend on the number of the hydrogen bonding points and the density of static charge since the adsorbing points are combined to the exposed hydrogen bonding points or the static charges on the material surface at a ratio of 1:1, so that it is difficult or impossible to artificially control the adsorbing amount of the surfactant.

Further, in order for a surfactant incorporated in the hydrophobic portion with designed molecular arrangement in order to display its function, a large amount of the surfactant is necessary, and moreover, the structure of the reforming layer containing such a functional group is frangible and easily broken. There are many reports on the cases where the functional group was released in the composite material to give adverse effect to the complex (for example, Japanese Patent Application Laid-open (KOKAI) Nos. 64-75581 and 57-92339).

It is also difficult to give a regularity to the orientation or arrangement of the surfactant molecules adsorbed on the material surface. Further, since the reforming layer makes effective use of hydrophobic bonding between the molecules in the hydrophobic portion (usually long-chain alkyl moiety), there is the structural restriction that the hydrophobic group is essentially composed of long-chain alkyl groups.

Still further, certain kinds of material to be treated are incapable of being surface-treated with a surfactant, and thus there has been the problem of limited scope of application.

Of the coupling agents, silane coupling agents have the disadvantage of being limited in the scope of application to the materials to be treated as in the case of surfactant. The silane coupling agents show excellent surface reforming effects for the siliceous materials such as glass, but are almost ineffective for improving the surface properties such as adsorptivity, of other materials. Also, the conditions for the surface treatment are delicate, and even a slight difference in conditions may result in forming a reforming layer different from the purposed one in properties such as adsorptivity and molecular orientation.

On the other hand, tetraalkyl titanate which is a kind of titanium coupling agent, has disadvantages in that it is rapidly hydrolyzed on contacting with water or humid air and is inconvenient to handling.

The technical problems of the present invention, therefore, is to provide a surface reforming agent which has a high adsorptivity, shows a strong adsorption and high molecular orientability and arrangeability on the surface of the material to be treated, and is also capable of desired surface treatment of a large variety of materials.

As a result of the present inventors' earnest studies for accomplishing the above-mentioned technical problems, it has been found that by dipping a material to be surface-treated in a treating solution prepared by dissolving a cone-type calix [4] resorcinarene compound represented by the formula (I) described later as an active ingredient of the surface reforming agent in a low-polarity organic solvent, it is possible to obtain the treated material in which the surface reforming agent is strongly combined at high molecular orientability and arrangeability, on the surface of the material. The present invention has been attained on the basis of this finding.

SUMMARY OF THE INVENTION

An object of the present invention is to provide a surface reforming agent which has a high adsorptivity, shows a strong adsorption and high molecular orientability and arrangeability on the surface of the material to be treated, is capable of desired surface treatment of a large variety of materials and has a wide scope of application, and a surface reforming method using the said agent.

Another object of the present invention is to provide a novel cone-type calix [4] resorcinarene compound comprising cyclic resorcin tetramer which is suited for use as an active ingredient of the surface reforming agent.

To accomplish the aims, in a first aspect of the present invention, there is provided a surface reforming agent comprising a cone-type calix [4] resorcinarene compound represented by the following formula (I):

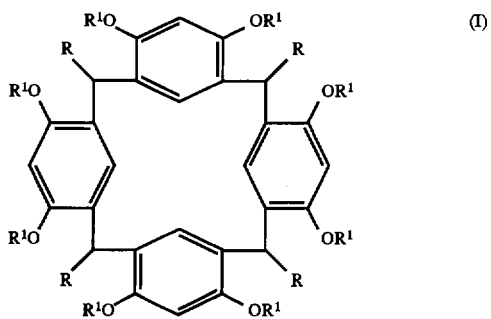

wherein R is an alkyl group having 3 to 18 carbon atoms, an alkenyl group having 3 to 18 carbon atoms, an aralkyl group having 3 to 18 carbon atoms or a substituted or non-substituted aryl group; $R^1$ is a hydrogen atom, a carboxyalkyl group in which the alkyl group has 1 to 3 carbon atoms, or a hydroxyalkyl group having 2 to 4 carbon atoms.

In a second aspect of the present invention, there is provided a surface reforming method which comprises contacting a material to be treated with a surface reforming agent comprising a cone-type calix [4] resorcinarene compound represented by the following formula (I):

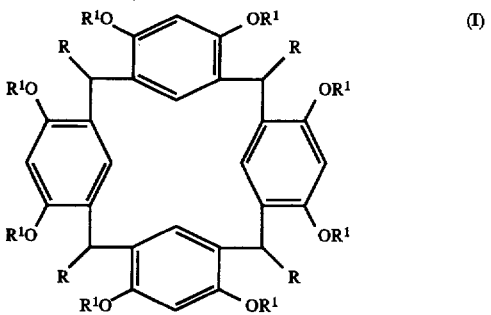

wherein R is an alkyl group having 3 to 18 carbon atoms, an alkenyl group having 3 to 18 carbon atoms, an aralkyl group having 3 to 18 carbon atoms or a substituted or non-substituted aryl group; $R^1$ is a hydrogen atom, a carboxyalkyl group in which the alkyl group has 1 to 3 carbon atoms, or a hydroxyalkyl group having 2 to 4 carbon atoms.

In a third aspect of the present invention, there is provided a surface-reformed material comprising a material to be treated and a surface reforming agent comprising a cone-type calix [4] resorcinarene compound represented by the following formula (I) adsorbed on the surface of the said material:

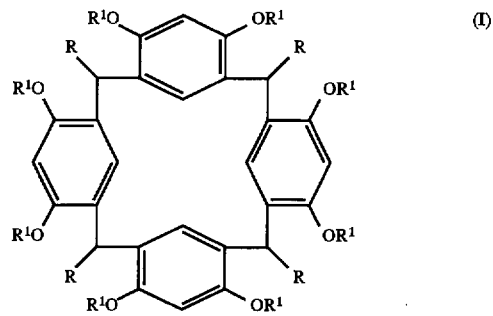

wherein R is an alkyl group having 3 to 18 carbon atoms, an alkenyl group having 3 to 18 carbon atoms, an aralkyl group having 3 to 18 carbon atoms or a substituted or non-substituted aryl group; $R^1$ is a hydrogen atom, a carboxyalkyl group in which the alkyl group has 1 to 3 carbon atoms, or a hydroxyalkyl group having 2 to 4 carbon atoms.

In a fourth aspect of the present invention, there is provided a cone-type calix [4] resorcinarene compound represented by the following formula (Ia):

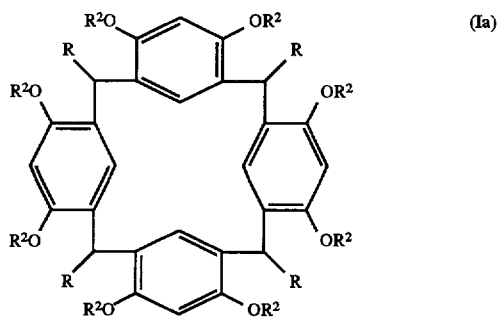

wherein R is an alkyl group having 3 to 18 carbon atoms, an alkenyl group having 3 to 18 carbon atoms, an aralkyl group having 3 to 18 carbon atoms, or a substituted or non-substituted aryl group; and $R^2$ is a carboxyalkyl group in which the alkyl group has 1 to 3 carbon atoms.

DETAILED DESCRIPTION OF THE INVENTION

Figure 1:
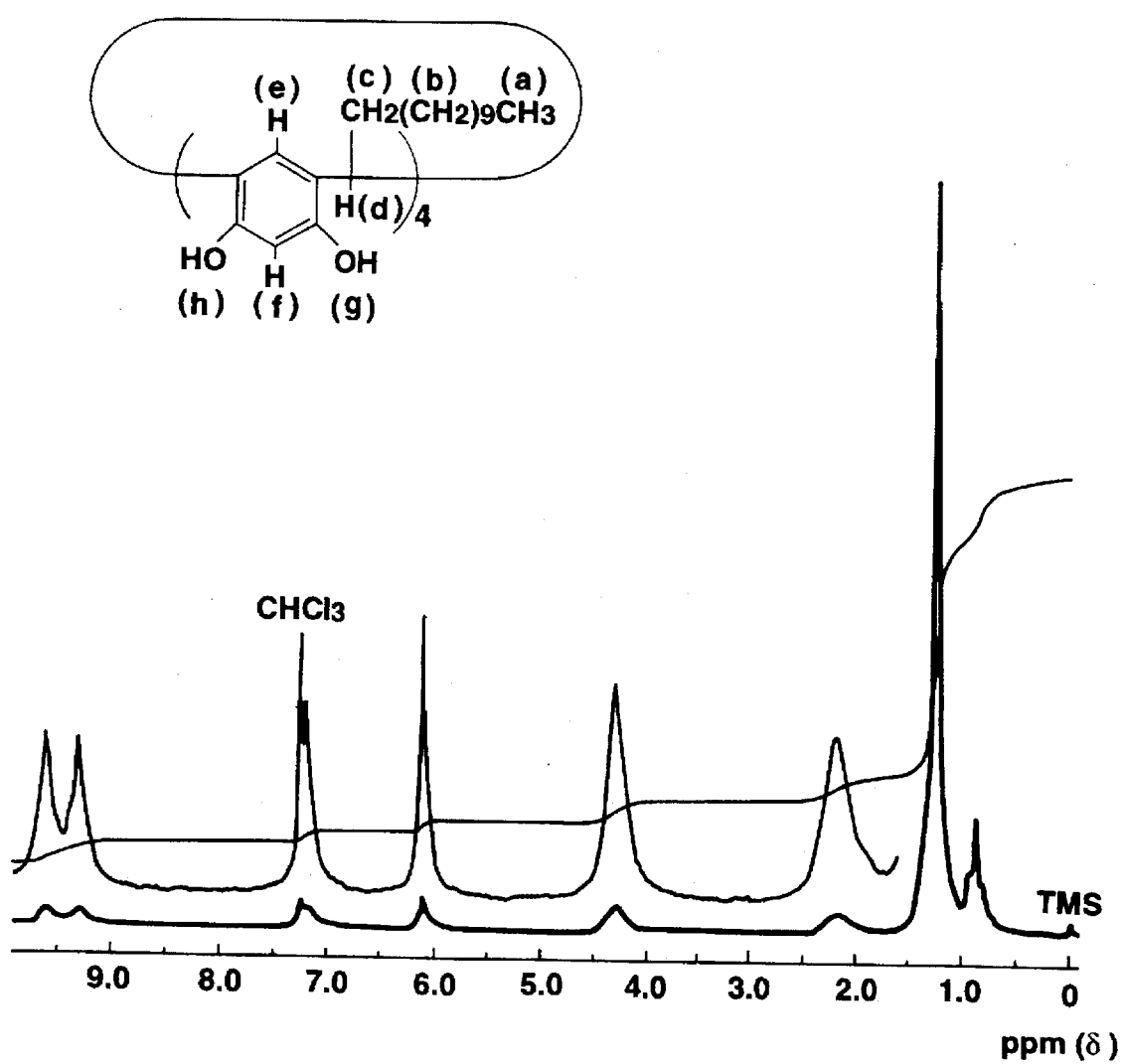
FIG. 1 shows the structural formula and $^1$H-NMR spectrum of a cone-type calix [4] resorcinarene compound represented by the formula (I) wherein R=$CH_3(CH_2)_{10}$ and $R^1$=H, obtained in Example 1.

In the cone-type calix [4] resorcinarene compounds represented by the formula (I) having a surface reforming-ability according to the present invention, R in the formula (I) should be an alkyl group having 3 to 18 carbon atoms, an alkenyl group having 3 to 18 carbon atoms, an aralkyl group having 3 to 18 carbon atoms, or a substituted or non-substituted aryl group for making the treated material surface hydrophobic. Such effects become stronger when R is an alkyl group having 8 to 18 carbon atoms, an alkenyl group having 8 to 18 carbon atoms or an aralkyl group having 8 to 18 carbon atoms. Alkyl, alkenyl and aralkyl groups may have substituents as far as the object of the present invention can be attained in use of the compound as a surface reforming agent.

Examples of the non-substituted aryl groups are phenyl, tolyl and naphthyl. As substituent, for example, an alkyl group having 1 to 18 carbon atoms and an alkenyl group having 1 to 18 carbon atoms can be used. The total number of carbon atoms is preferably 7 to 18 for making the treated material surface hydrophobic.

In order to provide the compounds with desired adsorptivity on the material surface to be treated, $R^1$ in the formula (I) should be a hydrogen atom, a carboxyalkyl group in which the alkyl group has 1 to 3 carbon atoms, or a hydroxyalkyl group in which the alkyl group has 2 to 4 carbon atoms. For further improving such properties, $R^1$ is preferably a carboxyalkyl group in which the alkyl group has 1 to 2 carbon atoms or a hydroxyalkyl group in which the alkyl group has 2 to 3 carbon atoms.

Among the cone-type calix [4] resorcinarene compounds represented by the formula (I) as a surface reforming agent according to the present invention, cone-type calix [4] resorcinarene compounds represented by the following formula (Ia) are novel:

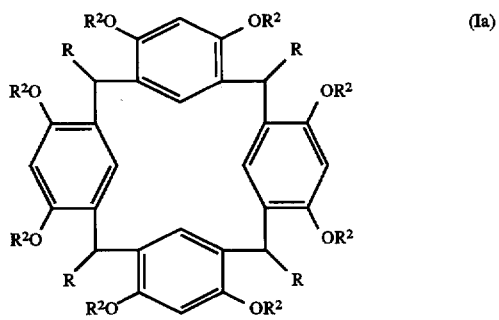
(Ia)

wherein R is an alkyl group having 3 to 18 carbon atoms, an alkenyl group having 3 to 18 carbon atoms, an aralkyl group having 3 to 18 carbon atoms, or a substituted or non-substituted aryl group; and $R^2$ is a carboxyalkyl group in which the alkyl group has 1 to 3 carbon atoms.

In the formula (Ia), it is preferred that R is an alkyl group having 8 to 18 carbon atoms, preferably an alkyl group having 8 to 15 carbon atoms, an alkenyl group having 8 to 18 carbon atoms, preferably an alkenyl group having 8 to 15 carbon atoms, an aralkyl group having 8 to 18 carbon atoms, preferably an aralkyl group having 8 to 15 carbon atoms; and $R^2$ is a carboxyalkyl group in which the alkyl group has 1 to 2 carbon atoms Some preferred examples of the cone-type calix [4] resorcinarene compounds represented by the formula (I) having a surface reforming-ability according to the present invention are shown below by chemical formula:

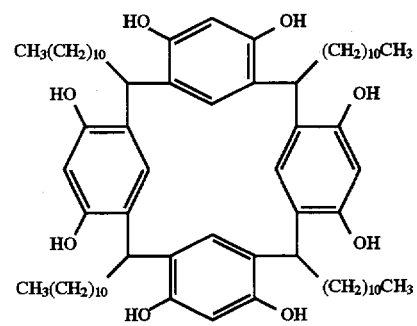

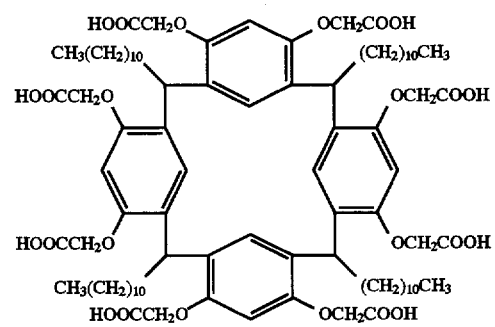

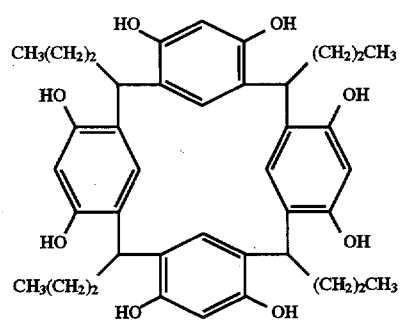

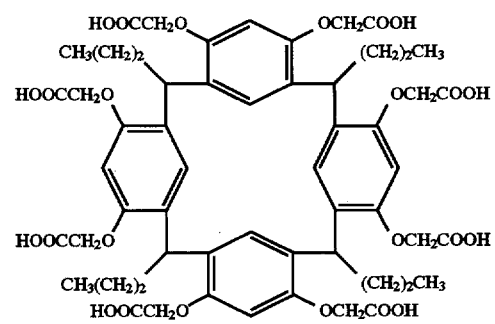

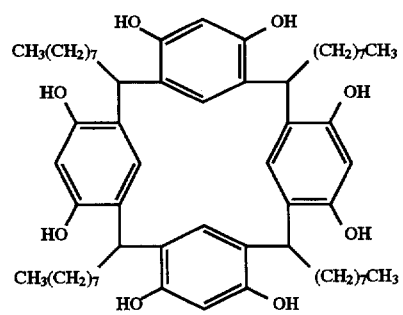

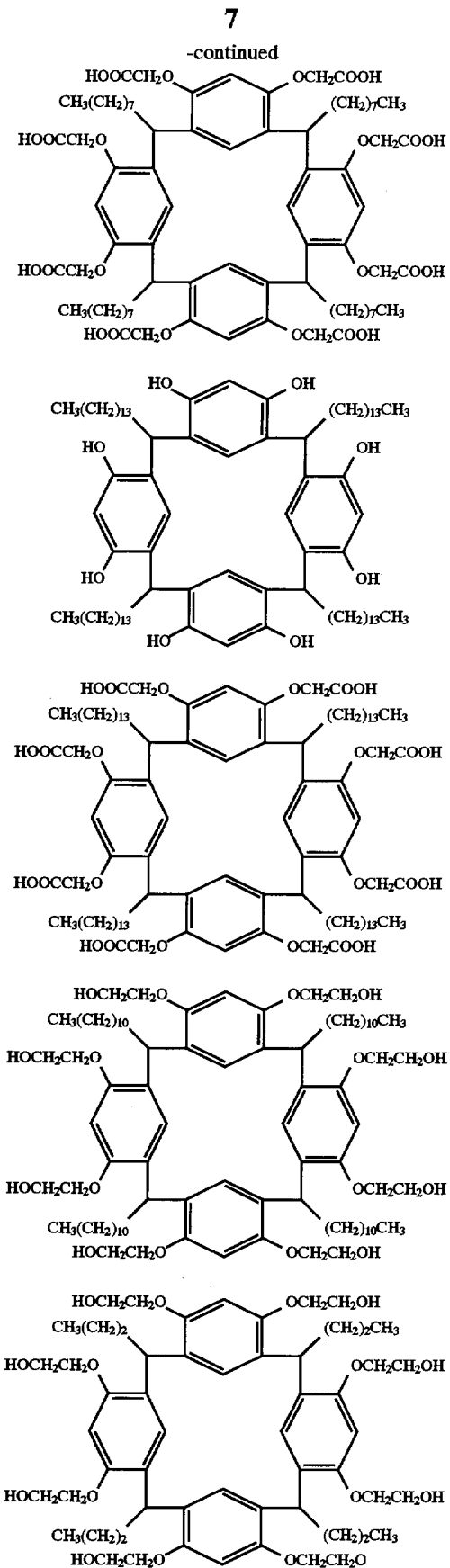

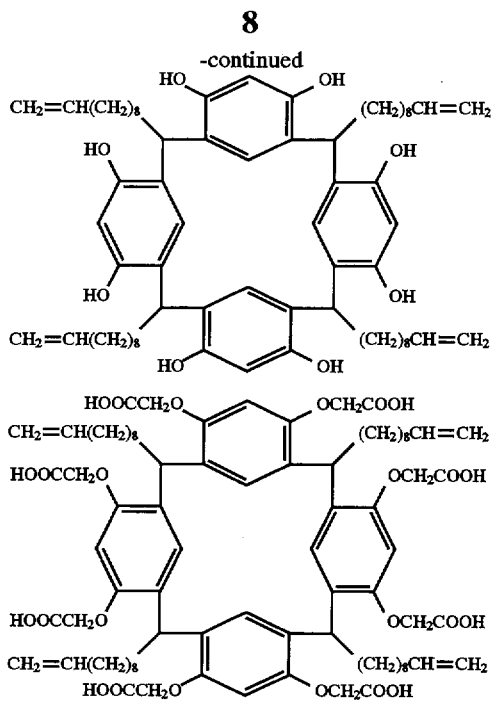

The cone-type calix [4] resorcinarene compounds represented by the formula (I) according to the present invention usually show white or yellow crystals at an ordinary temperature, and can be confirmed in the following way 1) or 2).

1) Kind and number of protons present in the molecule can be known from measurement of $^1$H-NMR spectrum.
2) Weight ratios of carbon, hydrogen, nitrogen, sulfur and halogen can be determined from elemental analysis. Weight ratio of oxygen can be calculated by subtracting the sum of weight ratios of the confirmed elements from 100.

The cone-type calix [4] resorcinarene compounds represented by the formula (I) according to the present invention can be synthesized from the following process.

Resorcinol and an aldehyde represented by the following formula:

R—CHO (wherein R is an alkyl having 3 to 18 carbon atoms, aralkyl having 3 to 18 carbon atoms or alkenyl group having 3 to 18 carbon atoms, a substituted or non-substituted aryl group, or a group into which the said alkyl, the said aralkyl, the said alkenyl group, or the said substituted or non-substituted aryl group can be introduced) are reacted under reflux in an inert gas (such as nitrogen gas) atmosphere in the presence of an acid catalyst such as hydrochloric acid, phosphoric acid, paratoluenesulfonic acid or the like by using an alcoholic solvent such as methanol, ethanol, isopropyl alcohol, methoxyethyl alcohol, ethoxyethyl alcohol or the like as reaction solvent.

The reactant ratio in the above reaction is usually 0.5 to 1.5 mole of aldehyde based on one mole of resorcinol, preferably equimolar to each other.

Reaction time is not shorter than 2 hours, preferably not shorter than 10 hours, more preferably 10 to 20 hours for obtaining objective cone-type calix [4] resorcinarene compounds represented by the formula (I) in a high yield.

In case where R is a group into which the said alkyl, the said aralkyl, the said alkenyl, or the said substituted or non-substituted aryl group has been introduced, the desired group is introduced by a known means after the above-mentioned reaction. For instance, a functional group having a double bond or a halogen at the terminal thereof is first introduced and then the portion of double bond or halogen is substituted with an appropriate functional group by known reactions.

In the surface reforming agent of the present invention, $R^1$ which provides the adsorption sites on the material to be treated can be introduced after the above reaction.

Introduction of this $R^1$, namely a carboxy($C_1$–$C_3$)alkyl group or a hydroxy($C_2$–$C_4$)alkyl group can be accomplished in a known way. For instance, introduction of a carboxy ($C_1$–$C_3$)alkyl group can be carried out by reacting the above reaction product with a ω-halocarboxylic acid ester in a polar solvent such as N,N-dimethylformamide (DMF) in the presence of a base such as potassium carbonate at 70° to 100° C. for 2 to 10 hours, and hydrolyzing the resulting reaction product.

Introduction of a hydroxy($C_2$–$C_4$)alkyl group can be carried out by reducing the reaction product with a reducing agent such as lithium aluminum hydride instead of hydrolysis reaction.

The cone-type calix [4] resorcinarene compounds represented by the formula (I) according to the present invention can be produced from a simple process in a high yield, and are therefore quite beneficial to the industries.

The methods for reforming the material surfaces by using the surface reforming agent according to the present invention are described below.

Among the reforming methods using the surface reforming agent of the present invention, the process comprising contacting the said surface reforming agent uniformly with the material surface is preferably employed with no particular restrictions.

The cone-type calix [4] resorcinarene compounds represented by the formula (I) according to the present invention are obtained in the form of crystal, and in use thereof, they may be applied in that form of crystal or in the form of solution.

A typical reforming method according to the present invention comprises (i) dipping the material in a treating solution in which a cone-type calix [4] resorcinarene compound represented by the formula (I) has been dissolved, (ii) spraying to the material of a treating solution in which a cone-type calix [4] resorcinarene compound represented by the formula (I) has been dissolved, or (iii) coating on the material with a solution in which a cone-type calix [4] resorcinarene compound represented by the formula (I) has been dissolved.

For dissolving the said cone-type calix [4] resorcinarene compounds represented by the formula (I), it is preferred to use an organic solvent capable of dissolving the said compounds and having a low polarity for allowing effective adsorption on the material to be treated. Typical examples of such low-polarity organic solvents are toluene, benzene, chloroform, xylene, methylene chloride, hexane and cyclohexane.

In order to elevate solubility of the said compounds, a polar solvent such as tetrahydrofuran (THF), acetone, alcohols or the like may be added to said organic solvent within limits not impairing adsorptivity of the compounds on the material to be treated.

The concentration of the cone-type calix [4] resorcinarene compounds represented by the formula (I) in the said treating solution may be usually on the order of $10^{-6}$ to $10^{-1}$ mol/liter, but in case a dense reforming layer is to be formed on the material surface, the said concentration is preferably in the range of $10^{-5}$ to $10^{-2}$ mol/liter.

The material to be treated with the reforming agent of the present invention is preferably one having a polar group in the surface. Typical examples of such material are powders, particles and moldings of a metal, a metal oxide, an inorganic substance or a resin, specifically metals such as iron, iron-based alloys, copper, copper-based alloys, titanium, titanium-based alloys, aluminum, aluminum-based alloys, nickel, nickel-based alloys, etc.; inorganic substances such as kaolin, talc, carbon black, molybdenum sulfide, gypsum, barium sulfate, lithium fluoride, calcium fluoride, zeolite, calcium phosphate, calcium carbonate, etc.; silicon dioxides such as silica and quartz; composite metal oxides composed of silicon dioxides; metal oxides such as iron oxide, zinc oxide, titania, alumina, ferrite, etc.; and resins such as polyvinyl alcohol, cellulose, polyamides, polyurethanes, polyimides, etc.

Among these substances, since silicon dioxides, iron oxides, ferrites and the like have strong surface polarity, the surface reforming agent is very strongly adsorbed thereon to provide a surface reformed material with high stability.

Especially, iron oxides or ferrites treated with the surface reforming agent of the present invention can be favorably used as magnetic particles constituting a magnetic toner.

The magnetic particles that can be effectively treated with the reforming agent of the present invention include hematite particles, magnetite [$FeO_x \cdot Fe_2O_3$ ($0<x\leqq1$)] particles, maghemite particles, particles produced by doping the above-mentioned particles with cobalt, particles produced by coating the above-mentioned particles with spinel ferrite such as Co-ferrite, etc. and the like.

The magnetic particles to be treated are preferably primary particles having a size of about 0.1 to 1.0 μm.

The content of the treated magnetic particles in magnetic toner is preferably 20 to 70% by weight. Binder resin used in magnetic toner is not specified, it is possible to use any suitable resins. For instance, styrene-based homopolymers such as polystyrene and poly-p-chlorostyrene; styrene-based copolymers such as styrene-p-chlorostyrene copolymer, styrene-propylene copolymer, styrene-vinyltoluene copolymer and styrene-acryl copolymer; polymethyl methacrylates; polyvinyl chloride; polyvinyl acetate; polyethylenes; polyesters, polyamides; epoxy resins and the like can be used as binder resin.

For the purpose of the present invention, it is satisfactory that the surface reforming agent comprising a cone-type calix [4] resorcinarene compound represented by the formula (I) according to the present invention form a layer at least one molecule size in thickness on the material surface.

What is most remarkable in the present invention is the fact that the surface reforming agent comprising a cone-type calix [4] resorcinarene compound represented by the formula (I) according to the present invention, in use for reforming treatment of the surface of a material, shows a high adsorptivity and a strong adsorption on the material surface, exhibits high molecular orientability and arrangeability on the material surface, can be applied to a large variety of material, and thus has a wide scope of application.

It is considered that the above fact is attributable to the characteristic three-dimensionally rigid molecular structure of the cone-type calix [4] resorcinarene compound represented by the formula (I) as an active ingredient of the surface reforming agent according to the present invention in which the molecule has a plurality of adsorption sites in one side and a plurality of chemical groups in the opposite side. That is, because one molecule has a plurality of adsorption sites, adsorptivity of the cone-type calix [4] resorcinarene compound represented by the formula (I) is increased regardless of the density of adsorption sites (provided by hydroxyl groups, electric charges, etc.) on the material surface, and further, each molecule can have a plurality of adsorption equilibrium at the same time, which helps to provide even stronger adsorption. And, when a close adsorption layer is formed, an interaction is produced due to hydrogen bonding between the molecules adsorbed on the material surface in addition to the interaction between the plural adsorption sites of the molecule and the material surface. These actions contribute to formation of a solid reforming layer with high orientability and arrangeability on the material surface.

The surface reforming agent comprising a cone-type calix [4] resorcinarene compound represented by the formula (I) according to the present invention, as described more particularly in the following Examples, has a high adsorptivity, shows a strong adsorption and high molecular orientability and arrangeability on the material surface, can be applied to a large variety of material, and has a wide scope of application, which indicates a high utility of the product of the present invention as a surface reforming agent.

Therefore, by simply applying the surface reforming agent of the present invention to a material having a polar surface, it is possible to form a very stable reformed surface on the material.

EXAMPLES

The present invention is described in further detail with reference to the examples. It is to be understood, however, that these examples are merely intended to illustrate the subject matter of the invention in a more definite way and not to be construed as limiting the scope of the invention.

In the following Examples and Comparative Examples, measurement of the UV spectra was made by using a spectrophotometer Model UV-320 (manufactured by Hitachi Corp.).

The contact angle was measured 30 seconds after dropping a determined amount of waterdrops onto a substrate to be treated, by using a contact angle meter Model CA-PF (manufactured by Kyowa Chemical Co., Ltd.).

Liquid crystal alignment was determined by holding a nematic liquid crystal (NPC-02 produced by Rodic Co., Ltd.) between a pair of surface reformed quartz plates and observing with a conoscope.

Example 1

A compound of the formula (I) wherein $R=CH_3(CH_2)_{10}$ and $R^1=H$ was synthesized from a known process (see Journal of American Chemical Socierty, Vol. 111, No. 14, pp. 5397–5404, 1989).

To a 50 ml three-necked flask equipped with a magnetic stirrer, a water-cooling condenser and a heater, 1.71 g of resorcinol in 20 ml of ethanol was supplied in a nitrogen gas stream, followed by addition of 2.85 g of dodecanal. Then 2.5 ml of a 12N HCl aqueous solution was added dropwise on an ice bath and the mixture was stirred under heating at 70° C. for 10 hours. The reaction solution was cooled to room temperature, whereby a yellow precipitate was obtained.

This yellow precipitate was suction filtered and washed with 2 liters of 80° C. hot water. After confirming that the filtrate ultimately became neutral, the obtained precipitate was dried at a temperature of 60° C. using a vacuum dryer.

The dried product was recrystallized twice with methanol, and then recrystallized with a hexane-acetone mixed solvent to produce white needle crystals in a yield of 78%.

Elemental analysis of the white needle crystal compound gave the measurements of C: 76.83%, H: 10.29%, which well agreed with the calculations of C: 76.96%, H: 10.23% for $C_{72}H_{112}O_8 \cdot H_2O$ (FW: 1123.69).

The result of measurement of $^1H$-NMR spectrum of the compound (measured by FT-NMR FX90Q of Japan Electron Co., Ltd.; δ: ppm; standard: tetramethylsilane; solvent: deuterated chloroform) is shown in FIG. 1.

A triplet corresponding to 12 protons appeared at 0.8 ppm. It may be assigned to 4 methyl groups (a). A peak corresponding to 72 protons appeared at 1.2 ppm. It can be assigned to methylene group (b) in the alkyl chain. Another peak corresponding to 8 protons was seen at 2.2 ppm. This can be assigned to methylene group (c) in the alkyl chain. A peak corresponding to 4 protons also appeared at 4.3 ppm. It can be assigned to methyne protons (d). Two singlets corresponding to 8 protons in all were admitted at 6.1 ppm and 7.2 ppm. They can be assigned to two protons (e) and (f) in the benzene ring. Singlets corresponding to 8 protons in all were observed at 9.3 ppm and 9.6 ppm. Since these singlets disappeared when heavy water was added, they can be assigned to protons (g) and (h) of hydroxyl groups in resorcinol.

The above results confirmed that the isolated product was a compound of the formula (I) wherein $R=CH_3(CH_2)_{10}$ and $R^1=H$, shown as the following formula. The melting point of this compound was 268° to 269° C.

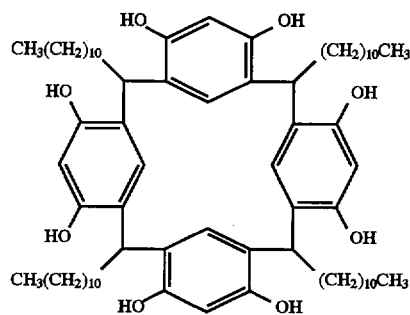

Example 2

1.0 g of the compound obtained in Example 1 was dissolved in 10 ml of DMF (N,N-dimethylformamide) and supplied into a 50 ml three-necked flask equipped with a magnetic stirrer, a water-cooling condenser and a heater. Then, 2.0 g of potassium carbonate and 1.6 ml of ethyl bromoacetate (each corresponding to about 2 equivalents to $R^1$ of the starting compound) were added and the resultant mixture was stirred under heating at 80° C. for 5 hours.

The objective substance was extracted from the reaction mixture with ether, washed with water and dried over saturated brine and anhydrous magnesium sulfate.

Ether was distilled away under reduced pressure from the dried solution to obtain slightly yellowish needle crystals.

These needle crystals had a melting point of 30° to 31° C. and their NMR spectrum confirmed $R^1=CH_2COOC_2H_5$. Yield was 89%.

1.0 g of this obtained compound was dissolved in 10 ml of ethanol and supplied into a 50 ml three-necked flask equipped with a magnetic stirrer, a water-cooling condenser and a heater, and then 0.5 g of potassium hydroxide (corresponding to about 2 equivalents to $R^1$ of the starting compound) was added. The produced white precipitate was dissolved by adding a proper amount of water. The solution was stirred under heating at 60° C. for one hour. When the pH of the solution of the reaction mixture was adjusted to 3.5 with a dilute hydrochloric acid aqueous solution, a white precipitate was obtained.

This precipitate was extracted with ether, washed with water, and dried over saturated brine and anhydrous magnesium sulfate.

Ether was distilled away under reduced pressure from the dried solution to obtain a white powder. Yield was 98%. Elemental analysis of the white powder compound gave the measurements of C: 64.99%, H: 8.31%, which well agreed with the calculations of C: 65.08%, H: 8.31% for $C_{88}H_{128}O_{24} \cdot 3H_2O$ (FW: 1624.03).

Figure 2:
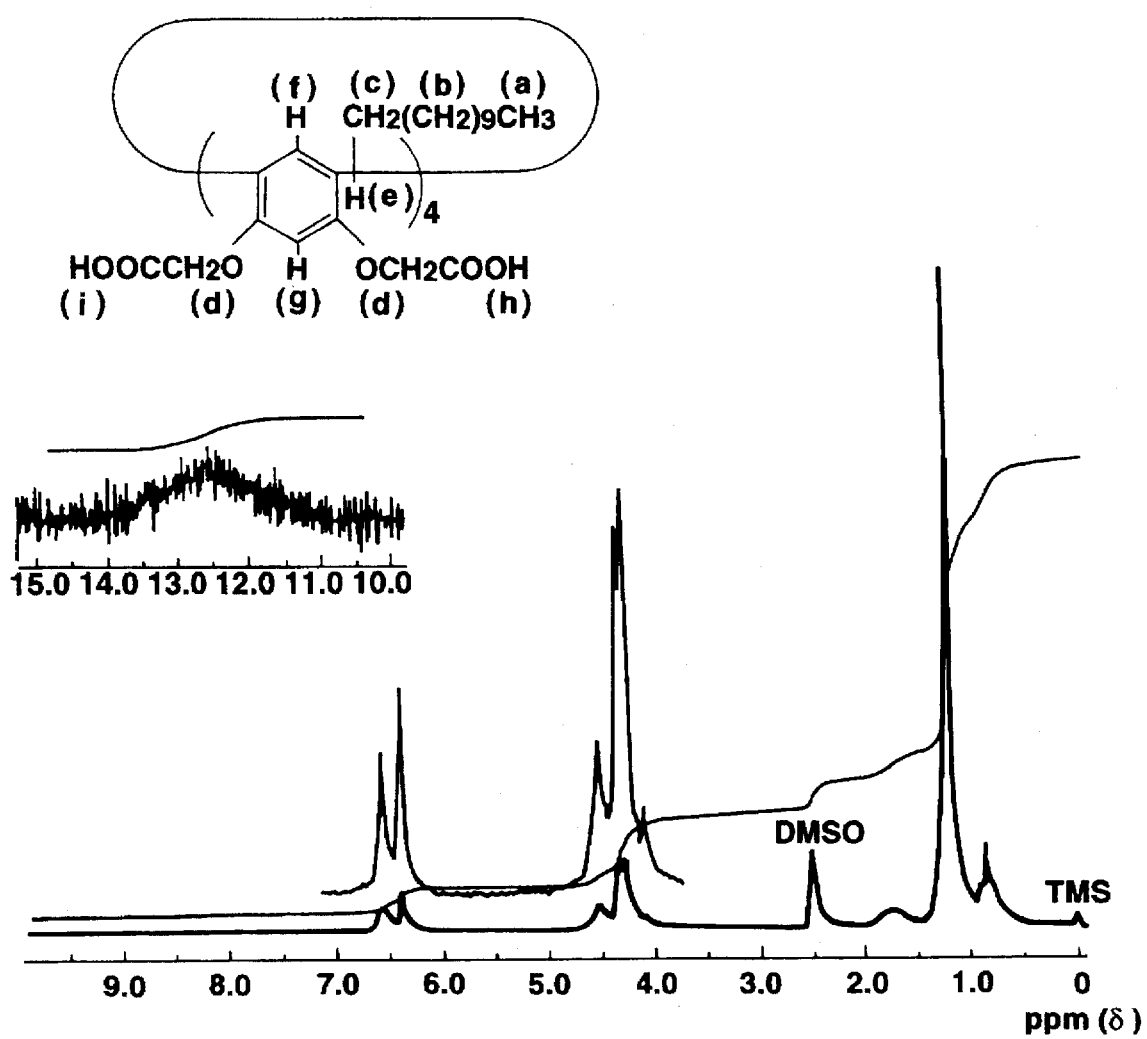
FIG. 2 shows the structural formula and $^1$H-NMR spectrum of a cone-type calix [4] resorcinarene compound represented by the formula (I) wherein R=$CH_3(CH_2)_{10}$ and $R^1$=$CH_2COOH$, obtained in Example 2.

The result of measurement of $^1$H-NMR spectrum (δ: ppm; standard: tetramethylsilane; solvent: deuterated DMSO) is shown in FIG. 2. The result of analysis was as follows.

A triplet corresponding to 12 protons appeared at 0.8 ppm. It can be assigned to 4 methyl groups (a). A peak corresponding to 72 protons appeared at 1.2 ppm. This can be assigned to methylene group (b) in the alkyl chain. Another peak corresponding to 8 protons was seen at 1.7 ppm. It can be assigned to methylene group (c) in the alkyl chain. Plural peaks corresponding to 20 protons also appeared at around 4.0 to 4.7 ppm. This may be accounted for as follows: due to the presence of asymmetric points in the molecule, the two protons of methylene group (d) become magnetically non-equivalent and manifest as doublets which overlap with the peak associated with methyne group (e) at 4.5 ppm. Two singlets corresponding 8 protons in all were admitted at 6.4 ppm and 6.6 ppm. They may be assigned to two protons (f) and (g) in the benzene ring. A peak corresponding to 8 protons was observed at 12.5 ppm. Since this peak disappeared when heavy water was added, it can be assigned to protons (h) and (i) of carboxylic acid.

From the above results, the isolated product was determined to be a compound of the formula (I) wherein R=CH$_3$(CH$_2$)$_{10}$ and $R^1$=CH$_2$COOH, shown as the following formula. The melting point of this compound was 174° to 175° C.

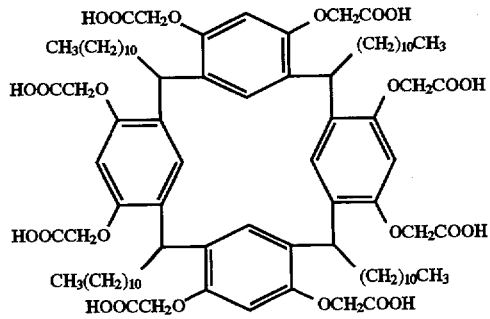

Example 3

To a 50 ml three-necked flask equipped with a magnetic stirrer, a water-cooling condenser and a heater, 1.71 g of resorcinol in 20 ml of ethanol was supplied in a nitrogen gas stream, followed by addition of 2.61 g of butanal. Then, 2.5 ml of 12N HCl aqueous solution was added dropwise on an ice bath and the resultant mixture was stirred under heating at 70° C. for 10 hours. The reaction solution was charged into 1 liter of water to obtain a yellow precipitate.

The yellow precipitate was suction filtered and washed with 2 liters of 80° C. hot water. After confirming that the filtrate ultimately became neutral, the obtained precipitate was dried at a temperature of 60° C. using a vacuum dryer.

The dried product was recrystallized with a chloroform-ethyl acetate mixed solvent and refined to obtain white granular crystals in a yield of 72%. Elemental analysis of the white granular crystal compound gave the measurements of C: 60.16%, H: 6.23%, Cl: 15.60% which well agreed with the calculations of C: 60.49%, H: 6.31%, Cl: 15.60% for $C_{40}H_{48}O_8 \cdot H_2O \cdot 1.2CHCl_3$ (FW: 818.09).

Figure 3:
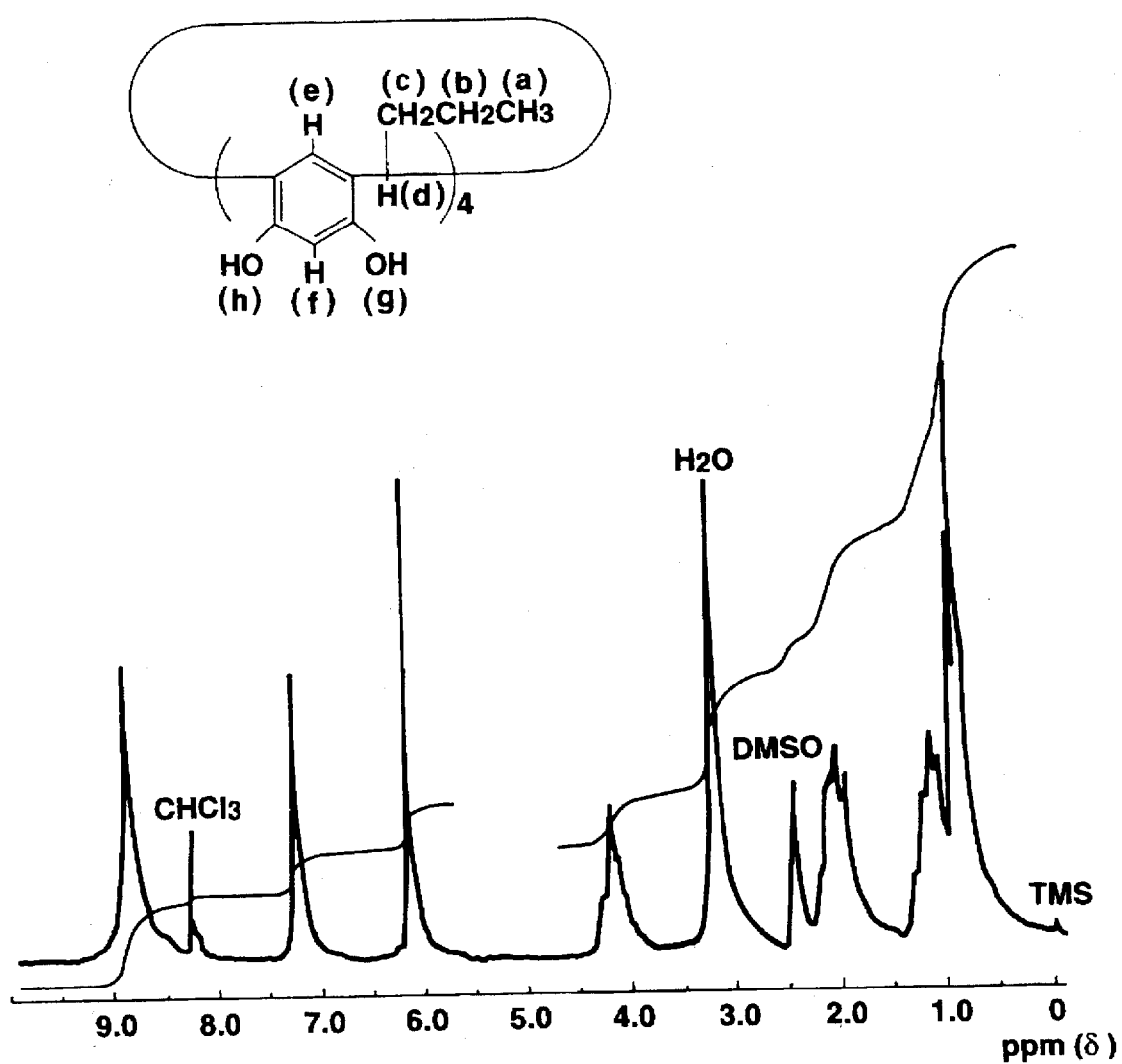
FIG. 3 shows the structural formula and $^1$H-NMR spectrum of a cone-type calix [4] resorcinarene compound represented by the formula (I) wherein R=$CH_3(CH_2)_2$ and $R^1$=H, obtained in Example 3.

The result of measurement of $^1$H-NMR spectrum (δ: ppm; standard: tetramethylsilane; solvent: deuterated DMSO) is shown in FIG. 3.

A triplet corresponding to 12 protons appeared at 0.8 ppm. It can be assigned to four methyl groups (a). A multiplet corresponding to 8 protons was admitted at 1.2 ppm. This can be assigned to methylene group (b) in the alkyl chain. A multiplet corresponding to 8 protons was appeared at 2.1 ppm. It can be assigned to methylene group (c) in the alkyl chain. A triplet corresponding to 4 protons was observed at 4.2 ppm. It can be assigned to proton (d) of methyne. Two singlets corresponding to 8 protons in all was recognized at 6.1 ppm and 6.3 ppm. They can be assigned to two protons (e) and (f) in the benzene ring. A singlet corresponding to 8 protons appeared at 8.9 ppm. Since it disappeared when heavy water was added, it can be assigned to protons (g) and (h) of hydroxyl group in the resorcinol. A singlet corresponding to approximately one proton appeared at 8.1 ppm is considered to be assignable to include chloroform.

The above results confirmed that the isolated product was a compound of the formula (I) wherein R=CH$_3$(CH$_2$)$_2$ and $R^1$=H, shown as the following formula. This compound had a melting point of 281°–282° C.

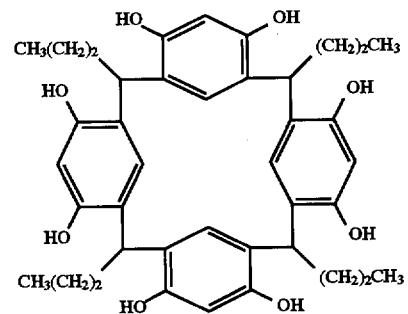

Example 4

The same process as Example 2 was carried out except for using the compound obtained in Example 3 as starting material.

Yield was 97%. Elemental analysis of the white powder crystal compound gave the measurements of C: 57.98%, H: 5.78%, which well agreed with the calculations of C: 58.13%, H: 5.92% for $C_{56}H_{64}O_{24} \cdot 2H_2O$ (FW: 1157.15).

Figure 4:
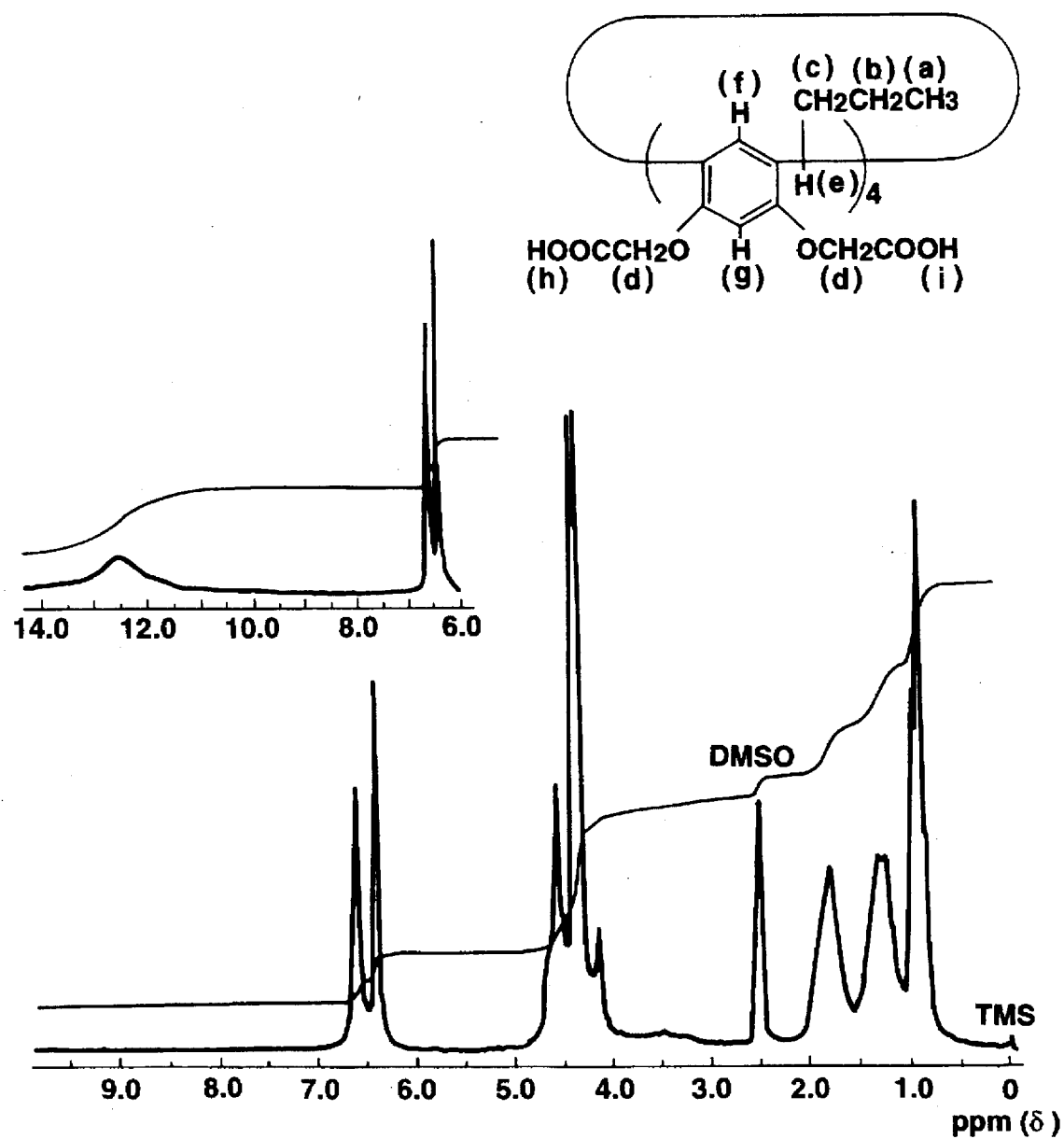
FIG. 4 shows the structural formula and $^1$H-NMR spectrum of a cone-type calix [4] resorcinarene compound represented by the formula (I) wherein R=$CH_3(CH_2)_2$ and $R^1$=$CH_2COOH$, obtained in Example 4.

The result of measure of $^1$H-NMR spectrum (δ: ppm; standard: tetramethylsilane; solvent: deuterated DMSO) is shown in FIG. 4.

A triplet corresponding to 12 protons appeared at 0.8 ppm. It can be assigned to four methyl groups (a). A peak corresponding 8 protons appeared at 1.2 ppm. This can be assigned to methylene group (b) in the alkyl chain. Another peak corresponding to 8 protons appeared at 1.7 ppm. This can be assigned to methylene group (c) in the alkyl chain.

Plural peaks corresponding to 20 protons appeared at around 4.0 to 4.7 ppm. This can be explained as follows: because of the presence of asymmetric points in the molecule, two protons of methylene group (d) became magnetically non-equivalent and manifested as doublets, and these doublets overlapped with the peak of methyne group (e) at 4.5 ppm. Two singlets corresponding to 8 protons in all were admitted at 6.4 ppm and 6.6 ppm. They may be assigned to two protons (f) and (g) in the benzene ring. A broad peak corresponding to 8 protons appeared at 12.5 ppm. Since it disappeared when heavy water was added, it can be assigned to carboxylic protons (h) and (i).

From the above results, the isolated compound was confirmed to be a compound of the formula (I) wherein $R=CH_3(CH_2)_2$ and $R^1=CH_2COOH$, shown as the following formula. The melting point of this compound was 209° to 210° C.

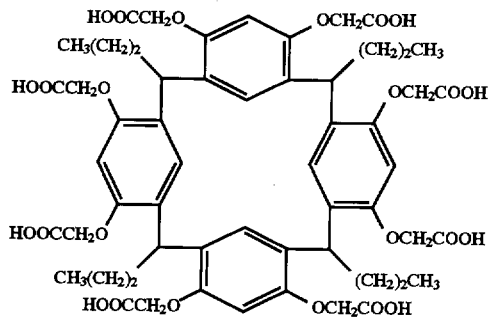

Example 5

22.5 mg of the compound of the formula (I) wherein $R=CH_3(CH_2)_{10}$ and $R^1=H$, obtained in Example 1, was dissolved in 20 ml (corresponding to $1.0\times10^{-3}$ mol/liter) of toluene, and a well cleaned quartz plate (1×3 cm) was dipped in the solution for 15 minutes.

The quartz plate was taken out, washed with toluene and dried.

The same operation was repeated several times by changing the solution concentration.

The adsorption amount was expressed by the apparent occupied area per adsorption molecule ($nm^2$/ molecule) calculated according to the Lambert-Beer's formula from UV spectrum absorbance of the adsorption compound and the absorption coefficient ($\epsilon=1.8\times10^4$ liter/mol.cm) of the compound, on the supposition of monomolecular layer.

Also, the contact angle of the treated quartz plate with a determined amount of waterdrop was measured.

Further, as a measure of orientation of the adsorbed molecules, liquid crystal was held between the treated substrates and observed by a conoscope to see whether homeotropic alignment of the liquid crystal (NPC-02) would be induced or not.

The results are shown in Table 1. As is seen from the table, the compound of the formula (I) wherein $R=CH_3(CH_2)_{10}$ and $R^1=H$ was well adsorbed on the quartz plate, and its adsorption amount was equal to the limiting area (1.2–1.4 $nm^2$/ molecule)of the π-A curve determined by an LB membrane device even at a low concentration of $10^{-5}$ mol/liter. The liquid crystal was induced homeotropic alignment even at a low adsorption amount. It was found that adsorption molecules were oriented perpendicular to the surface of the quartz plate and a dense monomolecular layer was formed thereof even at a low concentration.

Example 6

The same procedures as Example 5 was carried out except that 16.4 mg of the compound of the formula (I) wherein $R=CH_3(CH_2)_2$ and $R^1=H$, obtained in Example 3, was dissolved in 20 ml (corresponding to $1\times10^{-3}$ mol/liter) of toluene-THF (9:1 by volume) mixed solvent.

The results are shown in Table 1. It was found that self-assembly adsorption occurred and a dense monomolecular layer was formed thereon even in the absence of long alkyl chain.

Comparative Example 1

The same procedures as Example 5 were carried out except for using sodium 1,2-bis(2-ethylhexyloxycarbonyl) ethane sulfonate (hereinafter abbreviated as AOT). Adsorption amount could not be measured since AOT had no UV absorptivity. The angle of contact with water and the result of conoscopic observation on whether homeotropic alignment of liquid crystal was induced or not are shown in Table 1. The contact angle was small and the liquid crystal was not aligned, hence almost no adsorption of the compound (AOT) on the quartz plate.

Comparative Example 2

The same procedures as Example 5 were carried out except using a compound synthesized from 4-dodecylresorcinol as model monomer molecule. The results are shown in Table 1. The apparent occupied area per adsorption molecule was greater than 0.2 $nm^2$/molecule expected from the CPK model and the contact angle was also small. As for homeotropic alignment of the liquid crystal, only partial alignment took place more than one hour after the liquid crystal was held between the treating plates.

Comparative Example 3

The same procedures as Example 5 were carried out except using p-dodecylphenol as test compound. The results are shown in Table 1. Absorptivity coefficient was as low as about 1,600 and the adsorption amount was so small that it could not be determined. Also, the contact angle was small and the liquid crystal was not aligned.

Example 7

32.5 mg of the compound of the formula (I) wherein $R=CH_3(CH_2)_{10}$ and $R^1=CH_2COOH$, obtained in Example 2, was dissolved in 20 ml (corresponding to $1.0\times10^{-3}$ mol/liter) of toluene-THF (9:1 by volume) mixed solvent, and a well cleaned quartz plate (1×3 cm) was dipped in the solution for 15 minutes.

The quartz plate was taken out, washed with toluene and dried.

The same operation was repeated several times by changing the solution concentration.

The adsorption amount was expressed by apparent occupied area per adsorption molecule ($nm^2$/molecule) calculated according to the Lambert-Beer's formula from the UV spectrum absorbance of the adsorption compound and the absorption coefficient ($\epsilon=1.6\times10^4$ liter/mol.cm) of the compound, on the supposition of monomolecular layer.

Also, the contact angle of the treated quartz plate with a determined amount of waterdrop was measured.

Further, as a measure of orientation of the adsorbed molecules, liquid crystal was held between the treated substrates and observed by a conoscope to see whether homeotropic alignment of the liquid crystal (NPC-02) would be induced or not.

The results are shown in Table 2. As is seen from the table, the compound of the formula (I) wherein $R=CH_3(CH_2)_{10}$ and $R^1=CH_2COOH$ was well adsorbed on the quartz plate, and its adsorption amount was equal to the limiting area (1.6–1.8 nm$^2$/ molecule) of the π-A curve determined by an LB membrane device even at a low concentration of $10^{-6}$ mol/liter. Homeotropic alignment of liquid crystal was induced. It was found that adsorption molecules were oriented perpendicular to the surface of the quartz plate and a dense monomolecular layer was formed thereof even at a low concentration.

Comparative Example 4

The same procedures as Example 7 were carried out except for using a compound synthesized from 4-dodecylresorcinol with each of two hydroxyl groups thereof replaced by —OCH$_2$COOH as a model monomer molecule. The results are shown in Table 2. Although the obtained results are better than those of Comparative Example 2, the contact angle is still small and homeotropic alignment of liquid crystal is slow to take place.

Comparative Example 5

The same procedures as Example 7 were carried out except for using p-dodecylphenol with its hydroxyl group replaced by —OCH$_2$COOH. The results are shown in Table 2. Absorption coefficient was as low as 1,600 and the absorption amount was so small that it could not be determined. The contact angle was also small and no alignment of liquid crystal occurred.

Example 8

22.5 mg of the compound of the formula (I) wherein $R=CH_3(CH_2)_{10}$ and $R^1=H$, obtained in Example 1, was dissolved in 20 ml (corresponding to $1.0\times10^{-3}$ mol/liter) of toluene, and a quartz plate (1×3 cm$^2$) spin-coated with polyvinyl alcohol was dipped in the solution for 15 minutes. Thereafter, the quartz plate was taken out, washed with toluene and dried.

The adsorption ratio was expressed by the apparent occupied area per adsorption molecule (nm$^2$/ molecule) calculated according to the Lambert-Beer's formula from the UV spectrum absorbance of the adsorption compound and the absorption coefficient ($\epsilon=1.8\times10^4$ liter/mol.cm) of the compound, on the supposition of monomolecular layer. As a measure of orientability of the adsorbed molecules, the liquid crystal was held between the treated substrates and observed by a conoscope to see whether homeotropic alignment of the liquid crystal (NPC-02) was induced or not. The results are shown in Table 3. It was found that the compound was adsorbed as well as in Example 5.

Example 9

32.5 mg of the compound of the formula (I) wherein $R=CH_3(CH_2)_{10}$ and $R^1=CH_2COOH$, obtained in Example 1, was dissolved in 20 ml (corresponding to $1.0\times10^{-3}$ mol/liter) of toluene-THF (9:1 by volume) mixed solvent, and a well cleaned quartz plate (1×3 cm) spin-coated with polyvinyl alcohol was dipped in the solution for 15 minutes.

The quartz plate was taken out, washed with toluene and dried.

The adsorption ratio was expressed by the apparent occupied area per adsorption molecule (nm$^2$/ molecule) calculated according to the Lambert-Beer's formula from the UV spectrum absorbance of the adsorption compound and the absorption coefficient ($\epsilon=1.6\times10^4$ liter/mol.cm) of the compound, on the supposition of monomolecular layer.

Further, as a measure of orientation of the adsorbed molecules, liquid crystal was held between the treated substrates and observed by a conoscope to see whether homeotropic alignment of the liquid crystal (NPC-02) would be induced or not.

The results are shown in Table 3. As is seen from the table, it was found that adsorption molecules were oriented perpendicular to the surface of the polyvinyl alcohol film and a dense monomolecular layer was formed thereof even at a low concentration.

Comparative Example 6

The same procedures as Example 8 was carried out except for using a compound synthesized from 4-dodecylresorcinol as a model monomer molecule. The results are shown in Table 3. The liquid crystal could not be induced homeotropic alignment at all, which indicates poor molecular orientability of the compound.

Comparative Example 7

The same procedures as Example 9 was carried out except for using a compound synthesized from 4-dodecylresorcinol with each of two hydroxyl groups replaced by —OCH$_2$COOH as a model monomer molecule. The results are shown in Table 3. Molecular orientability of the compound was poor as in Comparative Example 6.

Example 10

The same procedures as Example 7 was carried out except that 23.1 mg of the compound of the formula (I) wherein $R=CH_3(CH_2)_2$ and $R^1=CH_2COOH$, was dissolved in 20 ml (corresponding to $1.0\times10^{-3}$ mol/liter) of a toluene-THF (9:1 by volume) mixed solvent.

The results are shown in Table 2. It is found that a dense monomolecular layer was formed even at a low concentration.

Example 11

The same procedures as Example 9 was carried out except that 23.1 mg of the compound of the formula (I) wherein $R=CH_3(CH_2)_2$ and $R^1=CH_2COOH$, was dissolved in 20 ml (corresponding to $1.0\times10^{-3}$ mol/liter) of a toluene-THF (9/1 by volume) mixed solvent.

The results are shown in Table 3. It is found that a dense monomolecular layer was formed on the surface of the polyvinyl alcohol film.

<Stability of Adsorption Layer>

In order to determine stability of the surface reforming layers formed by adsorbing the compounds of the present invention, each of the substrates treated with the compound solutions with a concentration of $10^{-3}$ mol/liter in the above Examples and Comparative Examples was washed with four polar solvents successively from one with lower polarity to one with higher polarity, namely with toluene, chloroform, THF and methanol in that order, and UV spectral measurement was made to see what solvent the adsorption layer is broken. The results are shown in Table 4. It is seen that the surface reforming agent comprising a compound of the present invention can form an adsorption layer with higher stability than that of the compounds of Comparative Examples.

This effect is considered attributable to the fact that the cone-type calix [4] resorcinarene compound used in the surface reforming agent according to the present invention have a number of adsorption sites in a molecule.

TABLE 1

Adsorption test on quartz substrate

| | Compound concentration (mol/l) | Apparent occupied area per adsorption molecule (nm²/molecule) | Contact angle (°) | Homeotropic alignment liquid crystal |
|---|---|---|---|---|
| Example 5 | $10^{-3}$ | 1.2 | 76 | ⊚ |
| | $10^{-4}$ | 1.4 | 75 | ⊚ |
| | $10^{-5}$ | 1.4 | 75 | ⊚ |
| | $10^{-6}$ | 3.4 | 64 | ⊚ |
| Example 6 | $10^{-3}$ | 1.2 | — | — |
| | $10^{-4}$ | 1.2 | — | — |
| | $10^{-5}$ | 1.4 | — | — |
| Comp. Example 1 | $10^{-3}$ | — | 35 | X |
| Comp. Example 2 | $10^{-3}$ | 0.5 | 47 | Δ |
| Comp. Example 3 | $10^{-3}$ | Unmeasurable | 46 | X |

(Note)
⊚: Rapid induced
○: Slow induced
Δ: Very slow induced
X: Not induced

TABLE 2

Adsorption test on quartz substrate

| | Compound concentration (mol/l) | Apparent occupied area per adsorption molecule (nm²/molecule) | Contact angle (°) | Homeotropic alignment liquid crystal |
|---|---|---|---|---|
| Example 7 | $10^{-3}$ | 1.6 | 77 | ⊚ |
| | $10^{-4}$ | 1.7 | 76 | ⊚ |
| | $10^{-5}$ | 1.7 | 74 | ⊚ |
| | $10^{-6}$ | 1.7 | 72 | ⊚ |
| Comp. Example 4 | $10^{-3}$ | 0.3 | 56 | ○ |
| Comp. Example 5 | $10^{-3}$ | unmeasurable | 57 | X |
| Example 10 | $10^{-3}$ | 1.6 | — | — |
| | $10^{-4}$ | 1.6 | — | — |
| | $10^{-5}$ | 1.7 | — | — |
| | $10^{-6}$ | 1.7 | — | — |

(Note)
⊚: Rapid induced
○: Slow induced
Δ: Very slow induced
X: Not induced

TABLE 3

Adsorption test to polyvinyl alcohol film

| | Apparent occupied area per adsorption molecule (nm²/molecule) | Homeotropic alignment liquid crystal |
|---|---|---|
| Example 8 | 1.3 | ⊚ |
| Example 9 | 1.7 | ⊚ |
| Comp. Example 6 | 0.30 | X |
| Comp. Example 7 | 0.30 | X |
| Example 11 | 1.7 | — |

(Note)
⊚: Rapid induced
○: Slow induced
Δ: Very slow induced
X: Not induced

TABLE 4

Stability of adsorption layer

| | Toluene | Chloroform | THF | Methanol |
|---|---|---|---|---|
| Example 5 | ○ | ○ | X | — |
| Comp. Example 2 | X | — | — | — |
| Example 7 | ○ | ○ | ○ | X |
| Comp. Example 4 | ○ | X | — | — |
| Example 8 | ○ | X | — | — |
| Comp. Example 6 | X | — | — | — |
| Example 9 | ○ | ○ | ○ | X |
| Comp. Example 7 | ○ | X | — | — |
| Example 10 | ○ | ○ | ○ | X |
| Example 11 | ○ | ○ | ○ | X |

(Note) ○: Not desorption
X: Desorption

Example 12

22.5 mg of the compound of the formula (I) wherein $R=CH_3(CH_2)_{10}$ and $R^1=H$, obtained in Example 1, was dissolved in 20 ml (corresponding to $1.0 \times 10^{-3}$ mol/liter) of toluene, and 1.0 g of black magnetite particles (EPT-1000, produced by Toda Kogyo Corp.) having a BET specific surface area of 3.7 m²/ g were added into 10 ml of the obtained solution, and ultrasonic wave was irradiated to the resultant solution for 15 minutes to disperse the magnetic iron oxide particles in the solution.

The obtained dispersion was subjected to centrifuge treatment to sediment the magnetic iron oxide particles.

The toluene supernatant was diluted 100 times with THF for measurement of the UV spectrum. The concentration of the supernatant was calculated according to the Lambert-Beer's formula from the UV spectrum absorbance and the absorption coefficient ($\epsilon=1.8 \times 10^4$ liter/mol.cm) of the compound, and the result was $4.9 \times 10^{-4}$ mol/liter).

From the difference between the concentration of the compound in the toluene solution before and after adsorption treatment, the adsorption amount on the iron oxide particles was calculated and the result was $5.1 \times 10^{-6}$ mol based on 1.0 g magnetic iron oxide particles. On the supposition of monomolecular layer, the adsorption amount expressed by the apparent occupied area per adsorption molecule (nm²/molecule) was 1.2 nm²/molecule.

The sedimented iron oxide particles were filtered out, washed with toluene and dried in vacuo at a temperature of 60° C. for 1 hour. After dried, the carbon content in the obtained iron oxide particles was measured by carbon/sulfur analyzer (EMIA-2200, manufactured by Horiba Co., Ltd.) and the result was 0.44 wt %. On the basis of the obtained carbon content, the apparent occupied area per adsorption molecule ($nm^2$/molecule) was calculated and the result was 1.2 $nm^2$/molecule.

As seen from the above, it was found that a uniform and dense monomolecular layer was formed on the surface of the black magnetic iron oxide particles.

Example 13

According to JIS K 5101, 0.5 g of the black magnetic iron oxide particles obtained in Example 12 and 0.5 cc of castor oil were kneaded into a paste by a Hoover muller. 4.5 g of clear lacquer was added to this paste and kneaded to form a coating material. This obtained coating material was applied on a cast-coated paper by using a 6-mil applicator to obtain a test piece. Gloss of this test piece was measured at an angle of incidence of 20° by using a digital gloss meter UGV-50 (manufactured by Suga Testing Machinary Co., Ltd.).

Measurement of gloss was made at the angle of incidence of 20° for the reason that the smaller the angle of incidence, the finer unevenness of the coating surface can be sensed, allowing more definite judgment of the degree of dispersion.

The results are shown in Table 5, along with the results of the similar test conducted on a non-treated black magnetic iron oxide particles (comparative specimen). The coating film formed by using the treated black magnetic iron oxide particles obtained in Example 12 obviously had a better gloss, indicating improved dispersibility by the above treatment. This coating film also had higher smoothness than the one formed by using the comparative specimen.

Example 14

Styrene-acryl copolymer (Hymer TB-1000, produced by Sanyo Chemical Industries, Ltd.): 100 parts by weight Black magnetic iron oxide powder treated in Example 12: 60 parts by weight Release agent (Biscol, produced by Sanyo Chemical Industries, Ltd.): 3 parts by weight A blend of the above composition was mixed up by a mixer, and then melted and kneaded by a hot two-roll mill for 10 minutes. The kneaded mixture was cooled, crushed, fine-milled and classified to obtain a magnetic toner having a volume-average diameter of 13-14 μm (measured by TA-11 manufactured by Coltor Counter Co., Ltd.).

95 parts by weight of an iron powder carrier (TEFV 200/300, produced by POWDERTECK Co., Ltd.) and 5 parts by weight of the obtained magnetic toner were mixed by a ball mill and the electric charging amount was measured by using TB-200 (manufactured by Toshiba Chemical Co., Ltd.) by blow-off method under a ordinary temperature (25° C.) and ordinary humidity (60%) condition. The electric charging rate was also measured under a low temperature and low humidity (15° C. and 10%) condition and under a high temperature and high humidity (30° C. and 90%) condition. The results are shown in Table 6 which also shows the results obtained with a magnetic toner prepared by using a non-treated black magnetic iron oxide particles (comparative specimen). It is seen that the magnetic toner containing the treated black magnetic iron oxide powder treated according to Example 12, as compared with the magnetic toner containing the non-treated black magnetic iron oxide particles, is higher in negative charging rate and also more stable against environmental changes. Thus, in this Example, there was obtained a magnetic toner with excellent electric charging properties and high stability.

TABLE 5

| Specimen | Gloss (%) |
|---|---|
| Particles obtained in Example 12 | 50 |
| Comparative specimen | 40 |

TABLE 6

| Measuring condition | | Charging amount (μc/g) | |
|---|---|---|---|
| Temperature | Humidity | Particles obtained in Example 12 | Comparative specimen |
| 25° C. | 60% | −24 | −18 |
| 15° C. | 10% | −24 | −21 |
| 30° C. | 90% | −23 | −14 |

What is claimed is:

1. A surface reforming composition comprising a cone-shaped calix [4] resorcinarene compound represented by the formula (I):

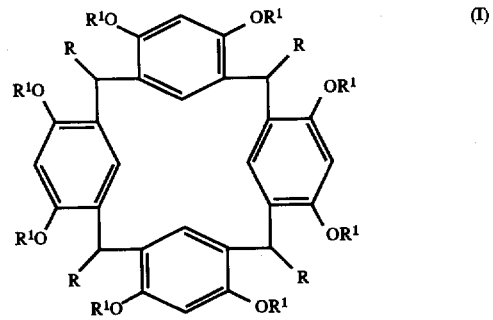

wherein R is an alkyl group having 3 to 18 carbon atoms, an alkenyl group having 3 to 18 carbon atoms, an aralkyl group having 3 to 18 carbon atoms or a substituted or non-substituted aryl group; $R^1$ is a carboxyalkyl group in which the alkyl group has 1 to 3 carbon atoms, or a hydroxyalkyl group having 2 to 4 carbon atoms.

2. A surface reforming composition according to claim 1, wherein in the formula (I) R is an alkyl group having 8 to 18 carbon atoms, an alkenyl group having 8 to 18 carbon atoms or an aralkyl group having 8 to 18 carbon atoms, and $R^1$ is a carbonyl group in which the alkyl group has 1 to 2 carbon atoms, or a hydroxyalkyl group having 2 to 3 carbon atoms.

3. A cone-shaped calix [4] resorcinarene compound represented by the formula (Ia):

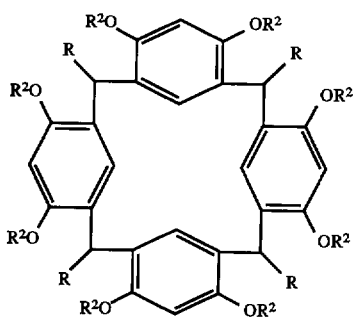

(Ia)

wherein R is an alkyl group having 3 to 18 carbon atoms, an alkenyl group having 3 to 18 carbon atoms, an aralkyl group having 3 to 18 carbon atoms, or a substituted or non-substituted aryl group; and $R^2$ is a carboxyalkyl group in which the alkyl group has 1 to 3 carbon atoms.

4. A cone-shaped calix [4] resorcinarene compound according to claim 3, wherein in the formula (Ia) R is an alkyl group having 8 to 18 carbon atoms, an alkenyl group having 8 to 18 carbon atoms or an aralkyl group having 8 to 18 carbon atoms.

5. A cone-shaped calix [4] resorcinarene compound according to claim 3, wherein in the formula (Ia) R is an alkyl group having 8 to 15 carbon atoms or an alkenyl group having 8 to 15 carbon atoms; and $R^2$ is a carboxyalkyl group in which the alkyl group has 1 to 2 carbon atoms.

6. A surface reforming composition comprising a cone-shaped calix [4] resorcinarene compound represented by the formula (Ia):

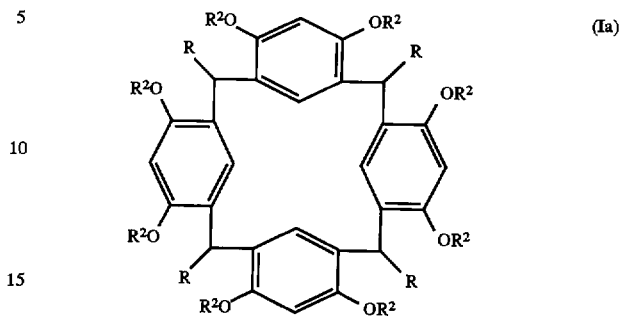

(Ia)

wherein R is an alkyl group having 3 to 18 carbon atoms, an alkenyl group having 3 to 18 carbon atoms, an aralkyl group having 3 to 18 carbon atoms, or a substituted or non-substituted aryl group; and $R^2$ is a carboxyalkyl group in which the alkyl group has 1 to 3 carbon atoms.

7. A surface reforming composition according to claim 1, wherein the formula (I) R is $-(CH_2)_{10}CH_3$, $-(CH_2)_2CH_3$, $-(CH_2)_7CH_3$, $-(CH_2)_{13}CH_3$ or $-(CH_2)_8CH=CH_2$, and $R^1$ is $-CH_2COOH$ or $-CH_2CH_2OH$.

* * * * *